United States Patent [19]
Buschmann et al.

[11] Patent Number: 5,811,582
[45] Date of Patent: Sep. 22, 1998

[54] DIMETHYL-(3-ARYL-BUT-3-ENYL)-AMINE COMPOUNDS AS PHARMACEUTICAL ACTIVE INGREDIENTS

[75] Inventors: Helmut Heinrich Buschmann, Aachen; Wolfgang Werner Alfred Strassburger, Wuerselen; Elmar Josef Friderichs, Stolberg; Babette-Yvonne Koegel, Langerwehe-Hamisch, all of Germany

[73] Assignee: Gruenenthal GmbH, Aachen, Germany

[21] Appl. No.: 820,377

[22] Filed: Mar. 12, 1997

[30] Foreign Application Priority Data

Mar. 13, 1996 [DE] Germany .................. 196 09 847.5

[51] Int. Cl.⁶ .................. C07C 215/00; C07C 69/76; A61K 31/135; A61K 31/235
[52] U.S. Cl. .................. 564/355; 560/64; 546/290; 544/162; 549/49; 549/74; 549/467; 548/182; 514/653; 514/533; 514/345; 514/237.8; 514/443; 514/438; 514/469; 514/369
[58] Field of Search .................. 514/653, 533, 514/345, 237.8, 443, 438, 469, 369; 564/355; 560/64; 546/290; 544/162; 549/49, 74, 467; 548/182

[56] References Cited

U.S. PATENT DOCUMENTS

| | | | |
|---|---|---|---|
| 3,956,348 | 5/1976 | Hilscher | 552/500 |
| 3,978,129 | 8/1976 | Welstead, Jr. | 564/355 |
| 4,173,649 | 11/1979 | Sundeen et al. | 514/653 |
| 4,354,154 | 10/1982 | Schiemann | 324/126 |
| 4,755,599 | 7/1988 | Barriere et al. | 540/544 |
| 5,527,821 | 6/1996 | Willman et al. | 514/428 |
| 5,539,120 | 7/1996 | Griffith et al. | 546/329 |

FOREIGN PATENT DOCUMENTS

| | | |
|---|---|---|
| 2409991 | 2/1974 | Germany . |
| 2409990 | 2/1975 | Germany . |

OTHER PUBLICATIONS

Dittert et al., "Acetaminophen Prodrugs I: Synthesis, Physicochemical Properties, and Analgesic Activity", *Journal of Pharmaceutical Sciences*, vol. 57, No. 5, May 1968, pp. 774–780.

Bundgaard et al., "A Novel Solution–Stable, Water–Soluble Prodrug Type for Drugs Containing a Hydroxyl or an NH–Acidc Group", *Journal of Medicinal Chemistry*, vol. 32, No. 12, Dec. 1989, pp. 2503–2507.

Welch, "Reduction of Aryl Diethyl Phosphates with Titanium Metal: A Method for Deoxygenation of Phenols", *J. Org. Chem.*, vol. 43, No. 25, 1978, pp. 4797–4799.

Olofsson et al., *Tetrahedron Letters*s, No. 18, pp. 1571–1574, 1977.

Raffa et al., "Opioid and Nonopioid Components Independently Contribute to the Mechanism of Tramadol, an 'Atypical' Opioid Analgesic", *The Journal of Pharmacology and Experimental Therapeutics*, vol. 260, No. 1, pp. 275–285, 1992.

Bundgaard, "Novel Chemical Approaches in Prodrug Design", *Drugs of the Future*, 1991, 16(5):443–458.

Thorberg et al., *J. Med. Chem.*, vol. 30, No. 11, 1989, pp. 2008–2012.

Jaffe et al., "Chapter 21: Opioid Analgesics and Antagonists" and Jaffe, Chapter 22: Drug Addiction and Drug Abuse, *Goodman and Gilman's: The Pharmacological Basis of Therapeutics*, Eighth Edition, Pergamon Press, pp. 485–573, 1990.

Winterfeldt, "Applications of Diisobutylaluminum Hydride (DIBAH) and Triisobutylaluminium (TIBA) as Reducing Agents in Organic Synthesis", *Synthesis*, Oct. 1975, pp. 617–630.

Hilscher, "Splitting of Steroid Ethers", *Chemical Abstracts*, vol. 84, 1976, Abstract No 84: 59862v, p. 567.

Raffa et al., "Complementary and Synergistic Antinociceptive Interaction between the Enantiomers of Tramadol", *Journal of Pharmacology and Experimental Therapeutics*, vol. 267, No. 1, pp. 331–340, 1993.

Nazarov et al., *Chemical Abstracts*, vol. 54, No. 20, Oct. 20, 1960, Abstract No. 20963c.

Hendershot et al., "Antagonism of the Frequency of Phenylquinone–induced Writhing in the Mouse by Weak Analgesics and Nonanalgesics", The Biochemical Research Laboratory, The Dow Chemical Company, Midland, Michigan, Sep. 1958.

Flick et al., *Arzneim. –Forsch./Drug Research*, 28(1) 1978, pp. 107–113.

Maurer et al., *Fresenius Z. Anal. Chem.*, (1984) 317:42–52.

Kato et al., *Chem. Pharm. Bull.*,32(6), pp. 2279–2289 (1984).

*Primary Examiner*—Deborah C. Lambkin
*Attorney, Agent, or Firm*—Evenson, McKeown, Edwards & Lenahan, PLLC

[57] ABSTRACT

Dimethyl-(3-aryl-but-3-enyl)-amine compounds, a method of preparing them, and the use of the compounds as pharmaceutical active ingredients are described.

6 Claims, No Drawings

DIMETHYL-(3-ARYL-BUT-3-ENYL)-AMINE COMPOUNDS AS PHARMACEUTICAL ACTIVE INGREDIENTS

This invention relates to dimethyl-(3-aryl-but-3-enyl)-amine compounds, to methods of preparing them, and to the use of these compounds in drugs.

The treatment of chronic and non-chronic pain conditions is of great importance in medicine. There is currently a world-wide need for additional pain therapy which is not exclusively opioid but which exhibits good efficacy. The pressing requirement for a target-oriented treatment of chronic and non-chronic pain conditions which is right for the patient, which is to be understood as the successful and satisfactory treatment of pain for the patient, is documented in the large number of scientific works which have recently appeared in the field of applied analgesics or on basic research on nociception.

Opioids have been used for many years as analgesics for the treatment of pain, even though they give rise to a series of side effects, for example addiction and dependency, respiratory depression, gastrointestinal inhibition effects and obstipation. They can therefore only be given over an extended period of time or in high dosages subject to special precautions, for example special prescription regulations (Goodman, Gilman, The Pharmaceutical Basis of Therapeutics, Pergamon Press, New York, 1990).

Tramadol hydrochloride—(1RS,2RS)-2-dimethylaminomethyl-1-(3-methoxy-phenyl)-cyclohexanol hydrochloride—assumes a special position amongst centrally acting analgesics, since this active ingredient acts as a strong inhibitor of pain without the side effects which are known for opioids (J. Pharmacol. Exptl. Ther. 267, 331 (1993)). Tramadol is a racemate and consists of equal amounts of (+) and (−) enantiomers. In vivo, this active ingredient forms the metabolite O-desmethyl-tramadol, which likewise exists as a mixture of enantiomers. Investigations have shown that both the enantiomers of tramadol and the enantiomers of the tramadol metabolite play a part in the analgesic effect (J. Pharmacol. Exptl. Ther. 260, 275 (1992)).

The underlying object of the present invention consisted of developing substances having an analgesic effect which are suitable for the treatment of severe pain without giving rise to the side effects which are typical of opioids.

The object was also that the substances to be developed should not exhibit the side effects which occur in some cases of treatment with tramadol, for example nausea and vomiting.

It has been found that the requirements imposed on the substances to be developed are fulfilled by certain dimethyl-(3-aryl-but-3-enyl)-amines. These substances are distinguished by a pronounced analgesic effect, which is significantly enhanced compared with tramadol.

The present invention accordingly relates to dimethyl-(3-aryl-but-3-enyl)-amine compounds of formula I

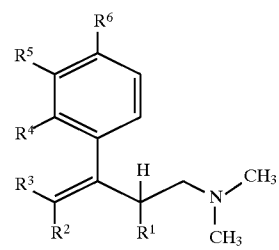

where $R^1$ is $C_{1-5}$ alkyl and $R^2$ denotes H or $C_{1-5}$ alkyl, or $R^1$ and $R^2$ together represent —$(CH_2)_{2-4}$—, —$(CH_2)_2$—$CHR^7$ or —$CH_2$—$CHR^7$—$CH_2$—, $R^3$ denotes H or $C_{1-5}$ alkyl, $R^4$ denotes H, OH, $C_{1-4}$ alkyl, O—$C_{1-4}$ alkyl, O-benzyl, $CF_3$, O—$CF_3$, Cl, F or $OR^8$, $R^5$ represents H, OH, $C_{1-4}$ alkyl, O—$C_{1-4}$ alkyl, O-benzyl, $CHF_2$, $CF_3$, O—$CF_3$, Cl, F or $OR^8$, and $R^6$ denotes H, OH, $C_{1-4}$ alkyl, O—$C_{1-4}$ alkyl, O-benzyl, $CF_3$, O—$CF_3$, Cl, F or $OR^8$, with the proviso that two of the radicals $R^4$, $R^5$ or $R^6$ are H, or $R^4$ and $R^5$ together denote —CH=C($R^9$)—O— or —CH=C($R^9$)—S—, with the proviso that $R^6$ is H, or $R^5$ and $R^6$ together denote —CH=CH—C($OR^{10}$)=CH—, with the proviso that $R^4$ is H, $R^7$ denotes $C_{1-8}$ alkyl, $C_{3-8}$ cycloalkyl, O—$C_{1-4}$ alkyl, O-benzyl, $CF_3$, Cl or F, $R^8$ denotes CO—$C_{1-5}$ alkyl, PO(O—$C_{1-4}$ alkyl)$_2$, CO—$C_6H_4$—$R^{11}$, CO(O—$C_{1-5}$ alkyl), CO—$CHR^{12}$—$NHR^{13}$, CO—NH—$C_6H_3$—$(R^{14})_2$ or an unsubstituted or substituted pyridyl, thienyl, thiazoyl or phenyl group, $R^9$ denotes H or $C_{1-4}$ alkyl, $R^{10}$ denotes H or $C_{1-3}$ alkyl, $R^{11}$ denotes OC(O)—$C_{1-3}$ alkyl in the ortho position or $CH_2$—N—$(R^{15})_2$ in the meta or para position, wherein $R^{15}$ denotes $C_{1-4}$ alkyl or both radicals $R^{15}$ form the 4-morpholino radical together with N, $R^{12}$ and $R^{13}$ are the same or different and denote H, $C_{1-6}$ alkyl or $C_{3-8}$ cycloalkyl, or $R^{12}$ and $R^{13}$ together denote —$(CH_2)_{3-8}$—, $R^{14}$ denotes H, OH, $C_{1-7}$ alkyl, O—$C_{1-7}$ alkyl, phenyl, O-aryl, $CF_3$, Cl or F, with the proviso that the two radicals $R^{14}$ are the same or different, in the form of their bases and/or salts of physiologically compatible acids, as enantiomers or racemates, with the proviso that the racemate of the compound of formula I, in which $R^1$ and $R^2$ together are —$(CH_2)_3$—, $R^3$, $R^4$ and $R^6$ denote H and $R^5$ is $OCH_3$, is excluded.

Preferred dimethyl-(3-aryl-but-3-enyl)-amine compounds correspond to formula I in which $R^1$ is $C_{1-3}$ alkyl and $R^2$ is H or $C_{1-3}$ alkyl, or $R^1$ and $R^2$ together represent —$(CH_2)_{2-4}$—, or —$(CH_2)_2$—$CHR^7$, $R^3$ denotes H or $C_{1-3}$ alkyl, $R^4$ denotes H, OH, $CF_3$, Cl, F or $OR^8$, $R^5$ represents H, OH, $C_{1-4}$ alkyl, O—$C_{1-4}$ alkyl, O-benzyl, $CHF_2$, $CF_3$, Cl, F or $OR^8$, and $R^6$ denotes H, OH, O—$C_{1-4}$ alkyl, O-benzyl, $CF_3$, Cl, F or $OR^8$, with the proviso that two of the radicals $R^4$, $R^5$ or $R^6$ are H, or $R^4$ and $R^5$ together denote —CH=C($R^9$)—O— or —CH=C($R^9$)—S—, with the proviso that $R^6$ is H, or $R^5$ and $R^6$ together denote —CH=CH—C($OR^{10}$)=CH—, with the proviso that $R^4$ is H, and $R^7$ denotes $C_{1-4}$ alkyl, $CF_3$, Cl or F. Dimethyl-(3-aryl-but-3-enyl)-amine compounds of formula I which are particularly suitable are those in which $R^1$ represents $CH_3$ or $C_3H_7$ and $R^2$ represents H, $CH_3$ or $CH_2CH_3$, or $R^1$ and $R^2$ together denote —$(CH_2)_{2-3}$— or —$(CH_2)_2$—$CHR^7$, $R^3$ denotes H, $CH_3$ or $CH_2CH_3$, $R^4$ denotes H or OH, $R^5$ denotes H, OH, $OCH_3$, $CHF_2$ or $OR^8$ and $R^6$ denotes H, OH or $CF_3$, with the proviso that two of the radicals $R^4$, $R^5$ or $R^6$ are H, or $R^4$ and $R^5$ together represent —CH═C($CH_3$)—S—, with the proviso that $R^6$ is H, or $R^5$ and $R^6$ together represent —CH═CH—C(OH)═CH—, with the proviso that $R^4$ is H, and $R^8$ represents CO—$C_6H_4$—$R^{11}$, where $R^{11}$ represents OC(O)—$C_{1-3}$ alkyl in the ortho position. Dimethyl-(3-aryl-but-3-enyl)-amine compounds are particularly preferred in which $R^1$ denotes $CH_3$ and $R^2$ denotes H or $CH_3$, or $R^1$ and $R^2$ together represent —($CH_2$)$_{2-3}$— or —($CH_2$)$_2$—CH($CH_3$)—, $R^3$ denotes H or $CH_3$, $R^4$ is H, $R^5$ denotes OH or $OR^8$, $R^6$ is H, and $R^8$ represents CO—$C_6H_4$—$R^{11}$, where $R^{11}$ represents OC(O)—$CH_3$ in the ortho position.

The present invention also relates to a method of preparing a dimethyl-(3-aryl-but-3-enyl)-amine compound of formula I, where $R^1$ is $C_{1-5}$ alkyl and $R^2$ denotes H or $C_{1-5}$ alkyl, or $R^1$ and $R^2$ together represent —($CH_2$)$_{2-4}$—, —($CH_2$)$_2$—$CHR^7$ or —$CH_2$—$CHR^7$—$CH_2$—, $R^3$ denotes H or $C_{1-5}$ alkyl, $R^4$ denotes H, $C_{1-4}$ alkyl, O—$C_{1-4}$ alkyl, O-benzyl, $CF_3$, O—$CF_3$, Cl or F, $R^5$ represents H, $C_{1-4}$ alkyl, O—$C_{1-4}$ alkyl, O-benzyl, $CHF_2$, $CF_3$, O—$CF_3$, Cl or F, and $R^6$ denotes H, $C_{1-4}$ alkyl, O—$C_{1-4}$ alkyl, O-benzyl, $CF_3$, O—$CF_3$, Cl or F, with the proviso that two of the radicals $R^4$, $R^5$ or $R^6$ are H, or $R^4$ and $R^5$ together denote —CH═C($R^9$)—O— or —CH═C($R^9$)—S—, with the proviso that $R^6$ is H, or $R^5$ and $R^6$ together denote —CH═CH—C($OR^{10}$)═CH—, with the proviso that $R^4$ is H, $R^7$ denotes $C_{1-8}$ alkyl, $C_{3-8}$ cycloalkyl, O—$C_{1-4}$ alkyl, O-benzyl, $CF_3$, Cl or F, $R^9$ denotes H or $C_{1-4}$ alkyl, and $R^{10}$ denotes H or $C_{1-3}$ alkyl, wherein the compound of formula I, in which $R^1$ and $R^2$ together denote —($CH_2$)$_3$—, $R^3$, $R^4$ and $R^6$ are H and $R^5$ is $OCH_3$, is excluded, which is characterised in that a β-dimethylaminoketone of formula II

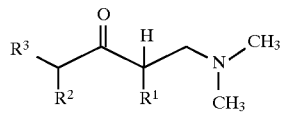

is reacted with an organometallic compound of formula III

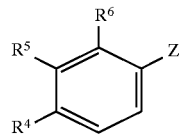

where Z denotes MgCl, MgBr, MgI or Li, to form a tertiary alcohol of formula IV

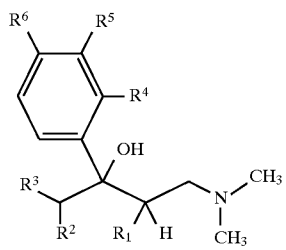

which is subsequently dehydrated to form a compound of formula I.

The reaction of a β-dimethylaminoketone with a Grignard compound of formula III, in which Z denotes MgCl, MgBr or MgI, or with an organolithium compound of formula III, can be conducted in an aliphatic ether, for example diethyl ether and/or tetrahydrofuran, at temperatures between −70° and +60° C. The reaction with a Grignard compound can be effected with or without the addition of a carrier reagent, preferably 1,2-dibromoethane. Organolithium compounds of formula III can be obtained by halogen/lithium exchange, by the reaction of a compound of formula III, in which Z denotes Cl, Br or I, with a solution of n-butyllithium in hexane, for example. The tertiary alcohols of formula IV which are obtained can be dehydrated with acids, particularly formic acid or hydrochloric acid, at temperatures between 0° and 100° C.

The present invention further relates to a method of preparing a dimethyl-(3-aryl-but-3-enyl)-amine compound of formula I, where $R^1$ is $C_{1-5}$ alkyl and $R^2$ denotes H or $C_{1-5}$ alkyl, or $R^1$ and $R^2$ together represent —($CH_2$)$_{2-4}$—, —($CH_2$)$_2$—$CHR^7$ or —$CH_2$—$CHR^7$—$CH_2$—, $R^3$ denotes H or $C_{1-5}$ alkyl, one of the radicals $R^4$, $R^5$ or $R^6$ denotes OH and the other two radicals are H, $R^7$ denotes $C_{1-8}$ alkyl, $C_{3-8}$ cycloalkyl, O—$C_{1-4}$ alkyl, O-benzyl, $CF_3$, Cl or F, which is characterised in that a compound of formula I, in which one of the radicals $R^4$, $R^5$ or $R^6$ denotes O—$CH_3$ and the other two radicals are H, is reacted with diisobutylaluminium hydride, or a compound of formula I, in which one of the radicals $R^4$, $R^5$ or $R^6$ denotes O-benzyl and the other two radicals are H, is reductively debenzylated.

The reaction of a dimethyl-(3-aryl-but-3-enyl)-amine compound with diisobutylaluminium hydride is usually conducted in an aromatic hydrocarbon, for example toluene, at a temperature between 60° and 130° C. (Synthesis 1975, 617; DE 24 09 990, DE 24 09 991; Chem. Abstr. 84, 59862 (1974)).

The reductive debenzylation of a compound of formula I according to the invention, in which one of the radicals $R^4$, $R^5$ or $R^6$ denotes O-benzyl, can be effected in the presence of platinum or palladium on a support material, for example activated carbon, in the presence of hydrogen in a solvent, for example acetic acid or a $C_{1-4}$ alkyl alcohol, at pressures between 1 and 100 bar and at temperatures between 20° and 100° C.

Dimethyl-(3-aryl-but-3-enyl)-amine compounds of general formula I, in which one or more of the aromatic substituents $R^4$, $R^5$ or $R^6$ denote $OR^8$ and $OR^8$ represents a phosphate, carbonate, carbamate, carboxylate, aryloxy or heteroaryloxy group, can be obtained by the reaction of a corresponding dimethyl-[3-(hydroxy-phenyl)-but-3-enyl]-amine compound of formula I in the form of an alkali salt, in which $R^4$, $R^5$ and/or $R^6$ represent an OH group, with a dialkyl chlorophosphate, with an alkyl chloroformate, with an aryl or heteroaryl isocyanate, with a carboxylic acid chloride or with an aryl or heteroaryl halide. These reactions are usually conducted in a solvent, for example toluene, dichloromethane, diethyl ether and/or tetrahydrofuran, at temperatures between −15° and +110° C. (Drugs of the Future 16, 443 (1991); J. Med. Chem. 30, 2008 (1989) and 32, 2503 (1989); J. Org. Chem. 43, 4797 (1978); Tetrahedron Lett. 1977, J. Pharm. Sci. 57, 774 (1968)). The reactions with an aryl or heteroaryl halide are carried out with the addition of copper powder and/or a copper(I) halide as a catalyst.

Dimethyl-(3-aryl-but-3-enyl)-amine compounds of formula I, in which $OR^8$ represents an α-aminocarboxylate group, can be obtained by the reaction of a corresponding dimethyl-[3-(hydroxy-phenyl)-but-3-enyl]-amine compound of formula I, in which $R^4$, $R^5$ and/or $R^6$ represent an OH group, with a corresponding 2-t-butoxycarbonyl-aminocarboxylic acid, using triethylamine and coupling reagents such as benzotriazol-1-yl-oxytripyrolidinophosphonium hexafluorophosphate in a solvent, for example dichloromethane.

The compounds of formula I can be converted, in the manner known in the art, into their salts with physiologically compatible acids, for example hydrochloric acid, hydrobromic acid, sulphuric acid, methanesulphonic acid, formic acid, acetic acid, oxalic acid, succinic acid, tartaric acid, mandelic acid, fumaric acid, lactic acid, citric acid, glutamic acid and/or aspartic acid. Salt formation is preferably conducted in a solvent, for example diethyl ether, diisopropyl ether, alkyl acetates, acetone and/or 2-butanone. Moreover, trimethylchlorosilane in aqueous solution is suitable for the preparation of hydrochlorides.

The compounds according to the invention have a pronounced analgesic effect and are toxicologically harmless. They are therefore suitable as pharmaceutical active ingredients. Accordingly, the present invention relates to the use of a dimethyl-(3-aryl-but-3-enyl)-amine compound of formula I according to claim 1 as an active ingredient in drugs, preferably as an active ingredient in pain-killing drugs.

In addition to at least one dimethyl-(3-aryl-but-3-enyl)-amine compound of formula I, drugs according to the invention contain support materials, fillers, solvents, diluents, colorants and/or binders. The selection of these auxiliary materials and of the amounts thereof to be used depends upon whether the drug is to be applied orally, intravenously, intraperitoneally, intradermally, intramuscularly, intranasally, buccally or locally, for example to infections of the skin, to the mucous membranes or to the eyes. Preparations in the form of tablets, dragees, capsules, granules, drops, juices and syrups are suitable for oral application. Solutions, suspensions, readily reconstitutable dry preparations and sprays are suitable for parenteral or topical application and for application by inhalation. Compounds according to the invention as a deposit in dissolved form or in a patch, optionally with the addition of agents which promote dermal penetration, are examples of suitable percutaneous forms of preparation. The compounds according to the invention can be released in a delayed manner from forms of preparations which can be applied orally or percutaneously.

The amount of active ingredient to be administered to the patient varies depending on the weight of the patient, on the type of application, on the indication and on the degree of severity of the illness. 10 to 500 mg per kg of at least one dimethyl-(3-aryl-but-3-enyl)-amine compound of formula I is usually administered.

EXAMPLES

Preparation of compounds according to the invention

The term "ether" denotes diethyl ether.

Silica gel 60 (0.040–0.063 mm) supplied by E. Merck, Darmstadt, was used as the stationary phase for column chromatography.

Thin-layer chromatography investigations were performed using prefabricated silica gel 60 F 254 HPTLC plates supplied by E. Merck, Darmstadt.

Racemate separations were performed on a Chiracel OD column supplied by Daicel Chemical Industries Ltd.

The mixture ratios of the mobile phases for all the chromatographic investigations are given as volume/volume.

Example 1

(Z)-(RS)-[3-(3-methoxy-phenyl)-2-methyl-pent-3-enyl]-dimethylamine hydrochloride (1)
1st step:
(2RS, 3RS)-1-dimethylamino-3-(3-methoxy-phenyl)-2-methyl-pentan-3-ol hydrochloride (2)
27.0 g (1.11 mole) of magnesium turnings were stirred in 150 ml tetrahydrofuran and 207.6 g (1.11 mole) 1-bromo-3-methoxy-benzene, dissolved in 400 ml tetrahydrofuran, were added drop-wise. The mixture was heated for one hour under reflux and was subsequently cooled to a temperature between 5° C. and 10° C. 128.30 g (0.89 mole) (RS)-1-dimethylamino-2-methyl-pentan-3-one, dissolved in 400 ml tetrahydrofuran, were added drop-wise at this temperature. The reaction mixture was allowed to stand and was subsequently cooled again to a temperature between 5° C. and 10° C. After adding 300 ml of 20 weight % ammonium chloride solution, the mixture was diluted with 400 ml ether. After phase separation the batch was extracted twice with ether, dried over sodium sulphate and the solvent was removed by distillation. The residue obtained was taken up in 3.2 l 2-butanone and treated with 120.60 g (1.11 mole) trimethylchlorosilane and 20 ml water. 121.5 g of hydrochloride (2) (38% theoretical) with a melting point of 198°–199° C. were obtained. 2nd step:
(Z)-(RS)-[3-(3-methoxy-phenyl)-2-methyl-pent-3-enyl]-dimethylamine hydrochloride (1)
200 g (0.69 mole) of hydrochloride (2) were dissolved in one litre of concentrated hydrochloric acid and allowed to stand at room temperature. The hydrochloric acid was removed by distillation under vacuum. The residue was dissolved in 1 l of ice-water and the pH was adjusted to 13 with 10 molar sodium hydroxide solution. After extraction with ether, drying the organic phase and removing the solvent by distillation, 162 g of crude product were obtained, and were purified by recrystallisation. 79 g (42% theoretical) of hydrochloride (1) with a melting point of 169°–170° C. were obtained.

Example 2

(Z)-(RS)-3-[1-(2-dimethylamino-1-methyl-ethyl)-propenyl]-phenol hydrochloride (3)
182 g (Z)-(RS)-[3-(3-methoxy-phenyl)-2-methyl-pent-3-enyl]-dimethylamine, dissolved in 360 ml toluene, were added drop-wise at room temperature to 1.6 l of a 20 weight % solution of diisobutylaluminium hydride in toluene. The mixture was then heated for 11 hours under reflux. After cooling to 0° C., 450 ml ethanol were added drop-wise with cooling. The mixture was then stirred for 15 minutes and diluted with 1 l toluene. Thereafter, 450 ml of an ethanol/water mixture (1:1) were added drop-wise with cooling. After stirring for one hour at room temperature, the precipitated aluminium hydroxide was filtered off under suction and the solvent was removed from the organic phase by distillation. 167 g (97.6% theoretical) of crude base were obtained, which were dissolved in 1.67 l acetone and treated with 65 ml of concentrated hydrochloric acid. 152 g (76% theoretical) of hydrochloride (3) crystallised out, and had a melting point of 161°–162° C.

Example 3

Enantiomers of (3):
(+)-(Z)-(S)-3-[1-(2-dimethylamino-1-methyl-ethyl)-propenyl]-phenol hydrochloride (+3)
and
(−)-(Z)-(R)-3-[1-(2-dimethylamino-1-methyl-ethyl)-propenyl]-phenol hydrochloride (−3)
The base was released with dichloromethane/aqueous sodium hydrogen carbonate solution from hydrochloride (3) obtained according to Example 2. After drying the solution, the dichloromethane was distilled off under vacuum. The racemate was then separated on a chiral HPLC column. The hydrochlorides, which had a melting point of 166°–167° C., were isolated from the enantiomers obtained, by reaction with concentrated hydrochloric acid in acetone.

(+3): yield: 42% theoretical
$[\alpha]^{RT}_D$=+3.6° (c=1.04; methanol)
(−3): yield: 44% theoretical
$[\alpha]^{RT}_D$=−3.6° (c=1.04; methanol)

Example 4

(Z)-(RS)-2-acetoxy-benzoic acid-3-[1-2-dimethylamino-1-methyl-ethyl)-propenyl]-phenyl ester hydrochloride (4)

The base was released with dichloromethane/aqueous sodium hydrogen carbonate solution from hydrochloride (3) prepared according to Example 2, and after drying the solution, the dichloromethane was removed by distillation. 0.67 g (3.0 mmole) of the base obtained were dissolved in 7 ml of dry dichloromethane and were treated at room temperature with 0.6 g (3.24 mmole) 2-acetyl-benzoyl chloride dissolved in 3 ml of dry dichloromethane. After stirring for 20 hours at room temperature, the reaction mixture was treated with 20 ml sodium hydrogen carbonate solution and the aqueous phase was extracted twice with 10 ml dichloromethane. The organic phases were combined and dried over sodium sulphate. After removing the solvent by distillation, 1.1 g of crude mixture were obtained and were introduced on to a column packed with silica gel. Elution with ether gave 0.68 g base, from which 0.68 g (54% theoretical) of hydrochloride (4), which had a melting point of 86°–88° C., was obtained with trimethylchlorosilane/water in ether.

Example 5

(E)-(RS)-[3-(3-methoxy-phenyl)-2-methyl-pent-3-enyl]-dimethylamine hydrochloride (5)

75 g (0.26 mole) (2RS,3RS)-1-dimethylamino-3-(3-methoxy-phenyl)-2-methyl-pentan-3-ol hydrochloride (1) from Example 1 (step 1) were dissolved in one litre of concentrated formic acid and heated for two hours under reflux. The formic acid was then distilled off under the vacuum from a water pump, and the residue was taken up in ice-water and treated with sodium hydroxide solution/ether. After drying the organic phase and removing the solvent by distillation, 60 g (98% theoretical) of crude base were obtained ((Z)-isomer (2):(E)-isomer (5)=6:4). The crude base was introduced on to a column packed with silica gel. Elution with 7:1 diisopropyl ether/methanol gave 20 g base, from which 18.4 g (26% theoretical) of hydrochloride (5), which had a melting point of 139°–140° C., was obtained with trimethylchlorosilane/water in 2-butanone.

Example 6

(E)-(RS)-3-[1-(2-dimethylamino-1-methyl-ethyl)-propenyl]-phenol hydrochloride (6)

The base was released with dichloromethane/sodium hydroxide solution from (5), which was prepared according to Example 5, and after drying the solution dichloromethane was removed by distillation. Hydrochloride (6), which had a melting point of 80° C., was obtained in a yield of 73% theoretical from the base obtained, under the conditions given in Example 2.

Example 7

Enantiomers of (6):
(+)-(E)-(R)-3-[1-(2-dimethylamino-1-methyl-ethyl)-propenyl]-phenol hydrochloride (+6)
and
(−)-(E)-(S)-3-[1-(2-dimethylamino-1-methyl-ethyl)-propenyl]-phenol hydrochloride (−6)

The base was released with dichloromethane/aqueous sodium hydrogen carbonate solution from hydrochloride (6) obtained according to Example 6. After drying the solution, the dichloromethane was distilled off under vacuum. The racemate was then separated on a chiral HPLC column. The hydrochlorides, which had a melting point of 154°–155° C., were isolated from the enantiomers obtained by reaction with concentrated hydrochloric acid in acetone.

(+6): yield: 42% theoretical
$[\alpha]^{RT}_D$=+36.3° (c=0.96; methanol)
(−6): yield: 44% theoretical
$[\alpha]^{RT}_D$=−33.7° (c=1.07; methanol)

Example 8

(Z)-(RS)-4-[1-(2-dimethylamino-1-methyl-ethyl)-propenyl]-phenol hydrochloride (7)

1st step:

(Z)-(RS)-[3-(4-methoxy-phenyl)-2-methyl-pent-3-enyl]-dimethylamine (8)

Starting from (RS)-1-dimethylamino-2-methyl-pentan-3-one and 1-bromo-4-methoxy-benzene, (2RS, 3RS)-1-dimethylamino-3-(4-methoxy-phenyl)-2-methyl-pentan-3-ol hydrochloride was obtained, under the conditions given in Example 1 (1st step), in a yield of 44% and with a melting point of 188°–189° C., and was converted with concentrated hydrochloric acid, under the conditions given in Example 1 (2nd step), into (Z)-(RS)-[3-(4-methoxy-phenyl)-2-methyl-pent-3-enyl]-dimethylamine (8). Compound (8) was obtained as a light yellow oil, in a yield of 46%.

2nd step:

(Z)-(RS)-4-[1-(2-dimethylamino-1-methyl-ethyl)-propenyl]-phenol hydrochloride (7)

Hydrochloride (7) was obtained, under the conditions given in Example 2, in a yield of 79% theoretical and with a melting point of 203° C. from the base obtained in step 1.

Example 9

(Z)-(RS)-dimethyl-(2-methyl-3-m-tolyl-pent-3-enyl) amine hydrochloride (9)

Starting from (RS)-1-dimethylamino-2-methyl-pentan-3-one and 3-bromo-toluene, (2RS, 3RS)-1-dimethylamino-2-methyl-3-(m-tolyl)-pentan-3-ol hydrochloride was obtained, under the conditions given in Example 1 (1st step), in a yield of 24% and with a melting point of 154°–155° C., and was converted with concentrated hydrochloric acid, under the conditions given in Example 1 (2nd step), into (Z)-(RS)-dimethyl-(2-methyl-3-m-tolyl-pent-3-enyl)-amine hydrochloride (9). Compound (9) was obtained in a yield of 36% (with respect to the alcohol used) and with a melting point of 172° C.

Example 10

(E)-(RS)-dimethyl-(2-methyl-3-m-tolyl-pent-3-enyl) amine hydrochloride (10)

Starting from (2RS, 3RS)-1-dimethylamino-2-methyl-3-(m-tolyl)-pentan-3-ol hydrochloride, which was obtained according to Example 9, hydrochloride (10) was obtained under the conditions given in Example 5 in a yield of 36% and with a melting point of 153° C.

Example 11

(Z)-(RS)-[3-(3-difluoromethyl-phenyl)-2-methyl-pent-3-enyl]-dimethylamine hydrochloride (11)

1st step:

(2RS,3RS)-3-(3-difluoromethyl-phenyl)-1-dimethylamino-2-methyl-pentan-3-ol hydrochloride (12)

7.0 g (34 mmole) 1-bromo-3-difluoromethyl-benzene, prepared from 3-bromobenzaldehyde and diethylaminosulphur trifluoride as described in Org. React. 35, 513 (1988), were dissolved in 110 ml of dry tetrahydrofuran and cooled to −75° C. After adding 34 mmole of a 1.6 molar n-butyllithium solution in hexane, the mixture was stirred for one hour at −75° C. 4.8 g (34 mmole) (2RS)-1-dimethylamino-2-methyl-pentan-3-one, dissolved in 15 ml of dry tetrahydrofuran, were then added drop-wise. The reaction mixture was warmed to room temperature over 2.5 hours. For the work-up, 65 ml of 5% hydrochloric acid were added drop-wise, whilst cooling in an ice bath, so that the internal temperature did not exceed 15° C. After phase separation, the organic phase was extracted with 40 ml of 5% hydrochloric acid. The combined aqueous phases were washed twice with 50 ml ether. The batch was treated with concentrated sodium hydroxide solution in order to release the base, and was extracted with dichloromethane. In this manner, 7.8 g of crude product were obtained, and were introduced on to a column packed with silica gel. Elution with 1:1 ethyl acetate/methanol gave 4.89 g of base, from which 4.6 g (44% theoretical) of hydrochloride (12), which had a melting point of 194°–195° C., was obtained with trimethylchlorosilane/water in 2-butanone.

2nd step:

(Z)-(RS)-[3-(3-difluoromethyl-phenyl)-2-methyl-pent-3-enyl]-dimethylamine hydrochloride (11)

10 g (32 mmole) (2RS,3RS)-3-(3-difluoromethyl-phenyl)-1-dimethylamino-2-methyl-pentan-3-ol hydrochloride (12) from step 1 were dissolved in 150 ml of concentrated formic acid and heated for two hours under reflux. The formic acid was then distilled off under the vacuum from a water pump, and the residue was taken up in ice-water and treated with sodium hydroxide solution/ether. After drying the organic phase and removing the solvent by distillation, 9.1 g (97% theoretical) of crude base were obtained, and were introduced on to a column packed with silica gel. Elution with 7:1 diisopropyl ether/methanol gave 3.0 g base, from which 2.3 g (24% theoretical) of hydrochloride (11), which had a melting point of 160°–161° C., were obtained with trimethylchlorosilane/water in 2-butanone.

Example 12

(Z)-(RS)-6-[1-(2-dimethylamino-1-methyl-ethyl)-propenyl]-naphth-2-ol hydrochloride (13)

Hydrochloride (13) was obtained, under the conditions given in Example 1 (2nd step), in a yield of 39% theoretical and with a melting point of 207°–208° C. from (1RS,2RS)-6-(3-dimethylamino-1-ethyl-1-hydroxy-2-methyl-propyl)-naphth-2-ol hydrochloride, prepared as described in Chirality, 6, 389 (1984).

Example 13

(E)-(RS)-[3-(3-methoxy-phenyl)-2-methyl-hex-3-enyl]-dimethylamine hydrochloride (14)
and
(Z)-(RS)-[3-(3-methoxy-phenyl)-2-methyl-hex-3-enyl]-dimethylamine hydrochloride (15)

Starting from (2RS)-3-dimethylamino-1-(3-methoxy-phenyl)-2-methyl-propan-1-one and 1-bromopropane, (2RS,3SR)-1-dimethylamino-3-(3-methoxy-phenyl)-2-methyl-hexan-3-ol hydrochloride (16) was obtained, under the conditions given in Example 1 (1st step) and using ether as a solvent, in a yield of 81% and with a melting point of 131°–132° C. 30 g (0.1 mole) of compound (16) were reacted with 450 ml of concentrated formic acid as in Example 5. The crude base (28 g) obtained in this manner, which consisted of a mixture of (Z)- and (E)-isomers, was introduced on to a column packed with silica gel. Elution with 7:1 diisopropyl ether/methanol gave 7 g base of the (E) compound (14) and 17 g base of the (Z) compound (15). The bases were converted into the hydrochlorides with trimethylchlorosilane/water in 2-butanone.

(14): yield: 5.9 g (21% theoretical) melting point: 154° C.
(15): yield: 15.8 g (56% theoretical) melting point: 110°–112° C.

Example 14

(E)-(RS)-3-[1-(2-dimethylamino-1-methyl-ethyl)-but-1-enyl]-phenol hydrochloride (17)

The base was released with dichloromethane/sodium hydroxide solution from (14), which was prepared as in Example 13, and after drying the solution the dichloromethane was removed by distillation. Hydrochloride (17) was obtained, under the conditions given in Example 2, from the base thus obtained, in a yield of 86% theoretical and with a melting point of 214° C.

Example 15

(Z)-(RS)-3-[1-(2-dimethylamino-1-methyl-ethyl)-but-1-enyl]-phenol hydrochloride (18)

The base was released with dichloromethane/sodium hydroxide solution from (15), which was prepared as in Example 13, and after drying the solution the dichloromethane was removed by distillation. Hydrochloride (18) was obtained, under the conditions given in Example 2, from the base thus obtained, in a yield of 86% theoretical and with a melting point of 120°–121° C.

Example 16

(RS)-[3-(3-methoxy-phenyl)-2-propyl-but-3-enyl]-dimethylamine hydrochloride (19)

Starting from (RS)-2-dimethylaminomethyl-1-(3-methoxy-phenyl)-pentan-1-one and methyl iodide, (2RS,3SR)-3-dimethylaminomethyl-2-(3-methoxy-phenyl)-hexan-2-ol hydrochloride (20) was obtained, under the conditions given in Example 1 (1st step) and using ether as a solvent, in a yield of 76% and with a melting point of 137°–138° C. 30 g (0.1 mole) of compound (20) were reacted with 300 ml of concentrated formic acid as in Example 5. The crude base obtained was introduced on to a column packed with silica gel. Elution with 7:1 diisopropyl ether/methanol gave 24 g base, from which 23.1 g (74% theoretical) of hydrochloride (19), which had a melting point of 120°–121° C., was obtained with trimethylchlorosilane/water in 2-butanone.

Example 17

(RS)-3-[1-(2-dimethylamino-1-methyl-ethyl]-vinyl]-phenol hydrochloride (21)

1st step:

(1RS,2SR)-3-(3-dimethylamino-1-hydroxy-1,2-dimethyl-propyl)-phenol hydrochloride (22)

Starting from (RS)-3-dimethylamino-1-(3-methoxy-phenyl)-2-methyl-propan-1-one and methyl iodide, (2RS, 3SR)-4-dimethylamino-2-(3-methoxy-phenyl)-3-methyl-butan-2-ol hydrochloride (23) was obtained, under the conditions given in Example 1 (1st step) and using ether as a solvent, in a yield of 46% and with a melting point of 178°–179° C. The base was released from (23) with dichloromethane/sodium hydroxide solution. After drying the solvent, the dichloromethane was distilled off under vacuum. 23.7 g (0.1 mole) of the base were reacted with diisobutylaluminium hydride as in Example 2. In this manner, 18.5 g (71% theoretical) of hydrochloride (22) were obtained with a melting point of 183°–184° C.

2nd step:

(RS)-3-[1-(2-dimethylamino-1-methyl-ethyl]-vinyl]-phenol hydrochloride (21)

10 g (37 mmole) of hydrochloride (22) from step 1 were dissolved in 150 ml of concentrated formic acid and heated for two hours under reflux. The formic acid was then distilled off under the vacuum from a water pump, and the residue was taken up in ice-water and treated with sodium hydroxide solution/ether. After drying the organic phase and removing the solvent by distillation, 9.1 g of crude base were obtained, from which 7.5 g (83% theoretical) of hydrochloride (21), which had a melting point of 228°–230° C., was obtained with concentrated hydrochloric acid in acetone.

Example 18

(RS)-3-[1-(2-dimethylamino-1-methyl-ethyl)-2-methyl-propenyl]-phenol hydrochloride (24)

1st step:

(RS)-[3-(3-methoxy-phenyl)-2,4-dimethyl-pent-3-enyl]-dimethylamine (25)

Starting from (RS)-1-dimethylamino-2,4-dimethyl-pentan-3-one and 1-bromo-3-methoxy-benzene, (2RS,3RS)-1-dimethylamino-3-(3-methoxy-phenyl)-2,4-dimethyl-pentan-3-ol hydrochloride (26) was obtained, under the conditions given in Example 1 (1st step), in a yield of 44% and with a melting point of 180°–181° C. 30 g (0.1 mole) of compound (26) were reacted with 450 ml of concentrated formic acid as in Example 5. The crude base obtained was introduced on to a column packed with silica gel. Elution with 7:1 diisopropyl ether/methanol gave 19 g base (77% theoretical) as a light yellow, viscous oil.

2nd step:

(RS)-3-[1-(2-dimethylamino-1-methyl-ethyl)-2-methyl-propenyl]-phenol hydrochloride (24)

Hydrochloride (24) was obtained from the base obtained in step 1, under the conditions given in Example 2, in a yield of 84% theoretical and with a melting point of 176°–177° C.

Example 19

(RS)-dimethyl-[2-(4-trifluoromethyl-phenyl)-cyclopent-2-enylmethyl]-amine hydrochloride (27)

(RS)-2-dimethylaminomethyl-cyclopentanone and 1-bromo-4-trifluoromethyl-benzene were reacted under the conditions given in Example 1 (1st step). 30 g of the crude product obtained were introduced on to a column packed with silica gel. Elution with 5:1 ethyl acetate/methanol gave 11.6 g base, which was converted with trimethylchlorosilane/water in 2-butanone into 12.0 g (21% theoretical) (1RS,2RS)-2-dimethylaminomethyl-1-(4-trifluoromethyl-phenyl)-cyclopentanol hydrochloride (28) with a melting point of 213°–214° C. 32.4 g (0.1 mole) of hydrochloride (28) were reacted with 450 ml of concentrated formic acid as in Example 5. The crude base obtained was introduced on to a column packed with silica gel. Elution with 7:1 diisopropyl ether/methanol gave 9.6 g base, which was converted with trimethylchlorosilane/water in 2-butanone into 8.9 g (29% theoretical) of hydrochloride (27) with a melting point of 219°–220° C.

Example 20

Enantiomers of (27):

(+)-(S)-dimethyl-[2-(4-trifluoromethyl-phenyl)-cyclopent-2-enylmethyl]-amine hydrochloride (+27)
and
(−)-(R)-dimethyl-[2-(4-trifluoromethyl-phenyl)-cyclopent-2-enylmethyl]-amine hydrochloride (−27)

The base was released from (27) with dichloromethane/sodium hydroxide solution. After drying the solution, the dichloromethane was distilled off under vacuum. The racemate was then separated on a chiral BPLC column. The hydrochlorides, which had a melting point of 244°–246° C., were prepared from the enantiomers obtained by reaction with concentrated hydrochloric acid in acetone.

(+27): yield: 42% theoretical
$[\alpha]^{RT}_D = +33.8°$ (c=1.00; methanol)
(−27): yield: 44% theoretical
$[\alpha]^{RT}_D = -34.3°$ (c=1.06; methanol)

Example 21

(RS)-2-(6-dimethylaminomethyl)-cyclohex-1-enyl)-phenol hydrochloride (29)

Starting from (RS)-2-dimethylaminomethyl-cyclohexanone and 1-bromo-2-methoxy-benzene, (1RS, 2RS)-2-dimethylaminomethyl-1-(2-methoxy-phenyl)-cyclohexanol hydrochloride (30) was obtained, under the conditions given in Example 1 (1st step) and using ether as a solvent, in a yield of 47%. The base was released from (30) with dichloromethane/sodium hydroxide solution. After drying the solution, the dichloromethane was distilled off under vacuum. 30.0 g (0.1 mole) of the base were reacted with diisobutylaluminium as in Example 2. 22.7 g (78% theoretical) (1RS,2RS)-2-(2-dimethylaminomethyl-1-hydroxy-cyclo-hexyl-phenol hydrochloride (31) were obtained, with a melting point of 168°–170° C. 28.6 g (0.1 mole) of compound (31) were reacted with 450 ml of concentrated formic acid as in Example 5. The crude base obtained was introduced on to a column packed with silica gel and eluted with 7:1 diisopropyl ether/methanol. 21 g base were obtained, from which 18.6 g (69% theoretical) of hydrochloride (29), which had a melting point of 168° C., was obtained with concentrated hydrochloric acid in acetone.

Example 22

Enantiomers of (29):

(−)-(R)-2-(6-dimethylaminomethyl)-cyclohex-1-enyl)-phenol hydrochloride (−29)
and
(+)-(S)-2-(6-dimethylaminomethyl)-cyclohex-1-enyl)-phenol hydrochloride (+29)

The base was released from (29) with dichloromethane/aqueous sodium hydrogen carbonate solution. After drying the solution, the dichloromethane was distilled off under vacuum. The racemate was then separated on a chiral BPLC column. The hydrochlorides, which had a melting point of 271°–272° C., were isolated from the enantiomers obtained, by reaction with concentrated hydrochloric acid in acetone.

(+29): yield: 43% theoretical
[α]$^{RT}_D$=+24.1° (c=0.96; methanol)
(−29): yield: 44% theoretical
[α]$^{RT}_D$=−23.5° (c=0.94; methanol)

Example 23

(RS)-dimethyl-[2-(4-trifluoromethyl-phenyl)-cyclohex-2-enylmethyl]-amine hydrochloride (32)

(RS)-2-dimethylaminomethyl-cyclohexanone and 1-bromo-4-trifluoromethyl-benzene were reacted under the conditions given in Example 1 (1st step). 30 g of the crude product were introduced on to a column packed with silica gel. Elution with 5:1 ethyl acetate/methanol gave 18.9 g base, which was converted with trimethylchlorosilane/water in 2-butanone into 16.4 g (37% theoretical) (1RS,2RS)-2-dimethylaminomethyl-1-(4-trifluoromethyl-phenyl)-cyclohexanol hydrochloride (33) with a melting point of 234° C. 33.7 g (0.1 mole) of hydrochloride (33) were reacted with 450 ml of concentrated formic acid as in Example 5. The crude base obtained was introduced on to a column packed with silica gel and eluted with 7:1 diisopropyl ether/methanol. 12.3 g base were obtained, and were converted with trimethylchlorosilane/water in 2-butanone into 10.4 g (32.5% theoretical) of hydrochloride (32) with a melting point of 205°–206° C.

Example 24

(RS)-dimethyl-[2-(2-methyl-benzo[b]thiophen-4-yl]-cyclohex-2-enylmethyl]-amine hydrochloride (34)

(RS)-2-dimethylaminomethyl-cyclohexanone and 4-bromo-2-methyl-benzo[b]thiophen were reacted under the conditions given in Example 1 (1st step), using ether as a solvent and 1,2-dibromoethane as a carrier reagent. 25 g of the crude product were introduced on to a column packed with silica gel. Elution with 1:1 ethyl acetate/methanol gave 12.6 g base, which was converted with trimethylchlorosilane/water in 2-butanone into 10.4 g (29% theoretical) (1RS,2RS)-2-dimethylaminomethyl-1-(2-methyl-benzo[b]thiophen-4-yl)-cyclohexanol hydrochloride (35) with a melting point of 204° C. 34.0 g (0.1 mole) of hydrochloride (35) were reacted with 450 ml of concentrated formic acid as in Example 5. The crude base (28.4 g) obtained in this manner was introduced on to a column packed with silica gel. Elution with ether gave 17.5 g base, which were converted with trimethylchlorosilane/water in 2-butanone into 15.2 g (54.8% theoretical) of hydrochloride (34) with a melting point of 179°–182° C.

Example 25

(−)-(3S,6R)-3-(6-dimethylaminomethyl-3-methyl-cyclohex-1-enyl)-phenol hydrochloride (−36)
and
(+)-(3R,6S)-3-(6-dimethylaminomethyl-3-methyl-cyclohex-1-enyl)-phenol hydrochloride (+36)

1st step:
(1RS,2RS,5SR)-2-dimethylaminomethyl-1-(3-methoxy-phenyl)-5-methyl-cyclohexanol hydrochloride (37)

95 ml (750 mmole) 1-bromo-3-methoxy-benzene were dissolved in 425 ml of dry tetrahydrofuran and cooled to −75° C. After adding 750 mmole of a 1.6 molar n-butyllithium solution in hexane, the mixture was stirred for one hour at −75° C. 82 g (484 mmole) (2RS,5SR)-2-dimethylaminomethyl-5-methyl-cyclohexanone, prepared from 3-methylcyclohexanone, dimethylamine hydrochloride and paraformaldehyde in glacial acetic acid, and dissolved in 120 ml of dry tetrahydrofuran, were then added drop-wise. The reaction mixture was warmed to room temperature over 2.5 hours. For the work-up, 200 ml water were added drop-wise, whilst cooling in an ice bath, so that the internal temperature did not exceed 15° C. After phase separation, the aqueous phase was extracted three times with 50 ml ethyl acetate. The combined organic phases were dried over sodium sulphate. After removing the solvent by distillation, the residue was dissolved in 700 ml acetone and treated with trimethylchlorosilane/water. 67 g (48% theoretical) of hydrochloride (37), which had a melting point of 173°–175° C., crystallised out at 4°–5° C.

2nd step:
Enantiomers of (37):
(+)-(1R,2R,5S)-2-dimethylaminomethyl-1-(3-methoxy-phenyl)-5-methyl-cyclohexanol hydrochloride (+37)
and
(−)-(1S,2S,5R)-2-dimethylaminomethyl-1-(3-methoxy-phenyl)-5-methyl-cyclohexanol hydrochloride (−37)

The base was released from (37) with dichloromethane/sodium hydroxide solution. After drying the solution, the dichloromethane was distilled off under vacuum. The racemate was then separated on a chiral HPLC column. The hydrochlorides, which had a melting point of 151°–153° C., were isolated from the enantiomers obtained by reaction with trimethylchlorosilane/water in 2-butanone.

(+37): yield: 43% theoretical
[α]$^{RT}_D$=+36.4° (c=1.01; methanol)
(−37): yield: 44% theoretical
[α]$^{RT}_D$=−37.7° (c=1.01; methanol)

3rd step:
(−)-(1R,4S)-[2-(3-methoxy-phenyl)-4-methyl-cyclohex-2-enylmethyl]-dimethylamine hydrochloride (−38)
and
(+)-(1S,4R)-[2-(3-methoxy-phenyl)-4-methyl-cyclohex-2-enylmethyl]-dimethylamine hydrochloride (+38)

The methoxy compounds (−37) and (+37) from the 2nd step were converted, under the conditions given in Example 5, into hydrochlorides (+38) and (−38) in a yield of 87% theoretical and with a melting point of 122°–123° C.

4th step:
(−)-(3S,6R)-3-(6-dimethylaminomethyl-3-methyl-cyclohex-1-enyl)-phenol hydrochloride (−36)
and
(+)-(3R,6S)-3-(6-dimethylaminomethyl-3-methyl-cyclohex-1-enyl)-phenol hydrochloride (+36)

Hydrochlorides (−36) and (+36) were obtained, under the conditions given in Example 2, from the bases obtained in step 3, by reaction with diisobutylaluminium hydride and subsequent precipitation of the hydrochloride with trimethylchlorosilane/water in 2-butanone, in a yield of 79% theoretical and with a melting point of 131°–133° C.

(−36): [α]$^{RT}_D$=−75.5° (c=0.96; methanol)
(+36): [α]$^{RT}_D$=+77.7° (c =1.08; methanol)

Example 26

(−)-(R)-3-(6-dimethylaminomethyl-cyclohex-1-enyl)-phenol hydrochloride (−39)

28.8 g (0.1 mole) (+)-(1R,2R)-3-(2-dimethylaminomethyl-1-hydroxy-cyclohexyl)-phenol hydrochloride were dissolved in 450 ml of concentrated formic acid and heated for two hours under reflux. The formic acid was then distilled off under the vacuum from a water pump and the base was released from the residue with dichloromethane/aqueous sodium carbonate solution. 21.8 g (81.4% theoretical) of hydrochloride (−39), which had a melting point of 216°–217° C., were obtained from the base by treatment with concentrated hydrochloric acid in acetone.

(−39): $[α]^{RT}_D = −96.6°$ (c=1.04; methanol)

Example 27

(+)-(S)-3-(6-dimethylaminomethyl-cyclohex-1-enyl)-phenol hydrochloride (+39)

21.8 g (81.4% theoretical) of hydrochloride (+39), which had a melting point of 216°–217° C., were obtained, under the conditions given in Example 26, from 28.8 g (0.1 mole) (−)-(1S,2S)-3-(2-dimethylaminomethyl-1-hydroxy-cyclohexyl)-phenol hydrochloride.

(+39): $[α]^{RT}_D = +89.9°$ (c=0.99; methanol)

Pharmacological Investigations

Testing for analgesia using the writhing test on mice

Testing for analgesic effectiveness was performed using the phenylquinone-induced writhing test on mice, modified according to I. C. Hendershot, J. Forsaith, J. Pharmacol. Exp. Ther. 125, 237–240 (1959). Male NMRI mice with a weight of 25–30 g were used for this purpose. For each dose of substance, groups of 10 animals received, 10 minutes after the intravenous administration of a compound according to the invention, 0.3 ml per mouse of an 0.02% aqueous solution of phenylquinone (phenylbenzoquinone: manufactured by Sigma, Deisenhofen; solution prepared with the addition of 5% ethanol and kept on a water bath at 45° C.) administered intraperitoneally. The animals were placed individually in observation cages. The number of pain-induced stretching movements (so-called writhing reactions=straightening of the body with stretching of the rear extremities) 5–20 minutes after the administration of phenylquinone was counted by means of a push-button counter.

The $ED_{50}$ values of the writhing reaction were calculated by means of regression analysis (evaluation program supplied by Martens EDV Service, Eckental) from the dose-dependent decrease in the writhing reactions, by comparison with groups of animals which were tested in parallel and to which no compounds according to the invention were administered.

All the compounds according to the invention which were tested exhibited a pronounced analgesic effect, which was enhanced by comparison with tramadol.

The results are summarised in the following Table.

TABLE

| Testing for analgesia using the writhing test on mice | |
|---|---|
| Compound according to the invention prepared according to Example | $ED_{50}$ (mg/kg) |
| 2 | 1.37 |
| 3 (+)-enantiomer | 2.25 |
| 3 (−)-enantiomer | 0.98 |
| 4 | 1.64 |
| 12 | 0.97 |
| 13 | 2.96 |
| 15 | 1.33 |
| 18 | 2.07 |
| 20 (+)-enantiomer | 1.40 |
| 20 (−)-enantiomer | 2.12 |
| 24 | 1.35 |
| 25 (−)-enantiomer | 0.90 |
| 26 (−)-enantiomer | 1.04 |
| 27 (+)-enantiomer | 1.60 |
| by comparison: tramadol | 3.68 |

We claim:

1. A dimethyl-(3-aryl-but-3-enyl)-amine compound corresponding to formula I

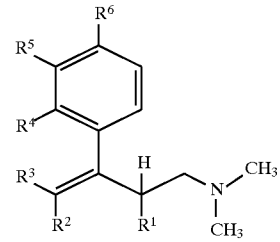

wherein $R^1$ is $C_{1-5}$ alkyl, and $R^2$ denotes H or $C_{1-5}$ alkyl, or $R^1$ and $R^2$ together represent —$(CH_2)_{2-4}$—, —$(CH_2)_2$—$CHR^7$— or —$CH_2$—$CHR^7$—$CH_2$—;

$R^3$ denotes H or $C_{1-5}$ alkyl;

$R^4$ denotes H, OH, $C_{1-4}$ alkyl, O—$C_{1-4}$ alkyl, O-benzyl, $CF_3$, O—$CF_3$, Cl, F or $OR^8$, $R^5$ represents H, OH, $C_{1-4}$ alkyl, O—$C_{1-4}$ alkyl, O-benzyl, $CHF_2$, $CF_3$, O—$CF_3$, Cl, F or $OR^8$, and $R^6$ denotes H, OH, $C_{1-4}$ alkyl, O—$C_{1-4}$ alkyl, O-benzyl, $CF_3$, O—$CF_3$, Cl, F or $OR^8$, with the proviso that two of the radicals $R^4$, $R^5$ or $R^6$ are H, or $R^4$ and $R^5$ together denote —CH=C($R^9$)—O— or —CH=C($R^9$)—S—, with the proviso that $R^6$ is H, or $R^5$ and $R^6$ together denote —CH=CH—C($OR^{10}$)=CH—, with the proviso that $R^4$ is H, $R^7$ denotes $C_{1-8}$ alkyl, $C_{3-8}$ cycloalkyl, O—$C_{1-4}$ alkyl, O-benzyl, $CF_3$, Cl or F, $R^8$ denotes CO—$C_{1-5}$ alkyl, PO(O—$C_{1-4}$ alkyl)$_2$, CO—$C_6H_4$—$R^{11}$, CO(O—$C_{1-5}$ alkyl), CO—$CHR^{12}$—$NHR^{13}$, CO—NH—$C_6H_3$—$(R^{14})_2$ or an unsubstituted or substituted pyridyl, thienyl, thiazoyl or phenyl group, $R^9$ denotes H or $C_{1-4}$ alkyl, $R^{10}$ denotes H or $C_{1-3}$ alkyl, $R^{11}$ denotes OC(O)—$C_{1-3}$ alkyl in the ortho position or $CH_2$—N—$(R^{15})_2$ in the meta or para position, wherein $R^{15}$ denotes $C_{1-4}$ alkyl or both radicals $R^{15}$ form the 4-morpholino radical together with N, $R^{12}$ and $R^{13}$ each independently represent H, $C_{1-6}$ alkyl or $C_{3-8}$ cycloalkyl, or $R^{12}$ and $R^{13}$ together denote —$(CH_2)_{3-8}$—, $R^{14}$ denotes H, OH, $C_{1-7}$ alkyl, O—$C_{1-7}$ alkyl, phenyl, O-aryl, $CF_3$, Cl or F, with the proviso that the two radicals $R^{14}$ are the same or different, or a salt thereof with a physiologically acceptable acid, as an isolated enantiomer or as a racemic mixture, with the proviso that the racemic mixture of the compound of formula I, in which $R^1$ and $R^2$ together represent —$(CH_2)_3$—; $R^3$, $R^4$ and $R^6$ each denote H; and $R^5$ is $OCH_3$, is excluded.

2. A dimethyl-(3-aryl-but-3-enyl)-amine compound according to claim 1, wherein $R^1$ is $C_{1-3}$ alkyl, and $R^2$ denotes H or $C_{1-3}$ alkyl, or $R^1$ and $R^2$ together represent —$(CH_2)_{2-4}$—, or —$(CH_2)_2$—$CHR^7$—;

$R^3$ denotes H or $C_{1-3}$ alkyl;

$R^4$ denotes H, OH, $CF_3$, Cl, F or $OR^8$, $R^5$ represents H, OH, $C_{1-4}$ alkyl, O—$C_{1-4}$ alkyl, O-benzyl, $CHF_2$, $CF_3$, Cl, F or $OR^8$, and $R^6$ denotes H, OH, O—$C_{1-4}$ alkyl, O-benzyl, $CF_3$, Cl, F or $OR^8$, with the proviso that two of the radicals $R^4$, $R^5$ and $R^6$ are H, or $R^4$ and $R^5$ together denote —CH=C($R^9$)—O— or —CH=C($R^9$)—S—, with the proviso that $R^6$ is H, or $R^5$ and $R^6$ together denote —CH=CH—C($OR^{10}$)=CH—, with the proviso that $R^4$ is H, and $R^7$ denotes $C_{1-4}$ alkyl, $CF_3$, Cl or F.

3. A dimethyl-(3-aryl-but-3-enyl)-amine compound according to claim 1, wherein $R^1$ represents $CH_3$ or $C_3H_7$, and $R^2$ represents H, $CH_3$ or $CH_2CH_3$, or $R^1$ and $R^2$ together denote —$(CH_2)_{2-3}$— or —$(CH_2)_2$—$CHR^7$—;

$R^3$ denotes H, $CH_3$ or $CH_2CH_3$;

$R^4$ denotes H or OH, $R^5$ denotes H, OH, $OCH_3$, $CHF_2$ or $OR^8$, and $R^6$ denotes H, OH or $CF_3$, with the proviso that two of the radicals $R^4$, $R^5$ and $R^6$ are H, or $R^4$ and $R^5$ together represent —CH=C($CH_3$)—S—, with the proviso that $R^6$ is H, or $R^5$ and $R^6$ together represent —CH=CH—C(OH)=CH—, with the proviso that $R^4$ is H, and $R^8$ represents CO—$C_6H_4$—$R^{11}$, where $R^{11}$ represents OC(O)—$C_{1-3}$ alkyl in the ortho position.

4. A dimethyl-(3-aryl-but-3-enyl)-amine compound according to claim 1, wherein $R^1$ denotes $CH_3$, and $R^2$ denotes H or $CH_3$, or $R^1$ and $R^2$ together represent —$(CH_2)_{2-3}$— or —$(CH_2)_2$—$CH(CH_3)$—;

$R^3$ denotes H or $CH_3$;

$R^4$ is H, $R^5$ denotes OH or $OR^8$, $R^6$ is H, and $R^8$ denotes CO—$C_6H_4$—$R^{11}$, where $R^{11}$ represents OC(O)—$CH_3$ in the ortho position.

5. A pharmaceutical composition comprising at least one pharmaceutical carrier or adjuvant and a pharmaceutically effective amount of a dimethyl-(3-aryl-but-3-enyl)-amine compound corresponding to formula I

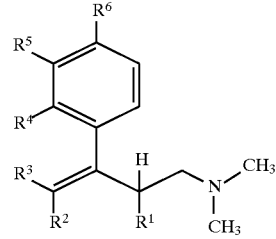

wherein $R^1$ is $C_{1-5}$ alkyl, and $R^2$ denotes H or $C_{1-5}$ alkyl, or $R^1$ and $R^2$ together represent —$(CH_2)_{2-4}$—, —$(CH_2)_2$—$CHR^7$— or —$CH_2$—$CHR^7$—$CH_2$—;

$R^3$ denotes H or $C_{1-5}$ alkyl;

$R^4$ denotes H, OH, $C_{1-4}$ alkyl, O—$C_{1-4}$ alkyl, O-benzyl, $CF_3$, O—$CF_3$, Cl, F or $OR^8$, $R^5$ represents H, OH, $C_{1-4}$ alkyl, O—$C_{1-4}$ alkyl, O-benzyl, $CHF_2$, $CF_3$, O—$CF_3$, Cl, F or $OR^8$, and $R^6$ denotes H, OH, $C_{1-4}$ alkyl, O—$C_{1-4}$ alkyl, O-benzyl, $CF_3$, O—$CF_3$, Cl, F or $OR^8$, with the proviso that two of the radicals $R^4$, $R^5$ or $R^6$ are H, or $R^4$ and $R^5$ together denote —CH=C($R^9$)—O— or —CH=C($R^9$)—S—, with the proviso that $R^6$ is H, or $R^5$ and $R^6$ together denote —CH=CH—C($OR^{10}$)=CH—, with the proviso that $R^4$ is H, $R^7$ denotes $C_{1-8}$ alkyl, $C_{3-8}$ cycloalkyl, O—$C_{1-4}$ alkyl, O-benzyl, $CF_3$, Cl or F, $R^8$ denotes CO—$C_{1-5}$ alkyl, PO(O—$C_{1-4}$ alkyl)$_2$, CO—$C_6H_4$—$R^{11}$, CO(O—$C_{1-5}$ alkyl), CO—$CHR^{12}$—$NHR^{13}$, CO—NH—$C_6H_3$—$(R^{14})_2$ or an unsubstituted or substituted pyridyl, thienyl, thiazoyl or phenyl group, $R^9$ denotes H or $C_{1-4}$ alkyl, $R^{10}$ denotes H or $C_{1-3}$ alkyl, $R^{11}$ denotes OC(O)—$C_{1-3}$ alkyl in the ortho position or $CH_2$—N—$(R^{15})_2$ in the meta or para position, wherein $R^{15}$ denotes $C_{1-4}$ alkyl or both radicals $R^{15}$ form the 4-morpholino radical together with N, $R^{12}$ and $R^{13}$ each independently represent H, $C_{1-6}$ alkyl or $C_{3-8}$ cycloalkyl or $R^{12}$ and $R^{13}$ together denote —$(CH_2)_{3-8}$—, $R^{14}$ denotes H, OH, $C_{1-7}$ alkyl, O—$C_{1-7}$ alkyl, phenyl, O-aryl, $CF_3$, Cl or F, with the proviso that the two radicals $R^{14}$ are the same or different, or a salt thereof with a physiologically acceptable acid, as an isolated enantiomer or as a racemic mixture, with the proviso that the racemic mixture of the compound of formula I, in which $R^1$ and $R^2$ together represent —$(CH_2)_3$—; $R^3$, $R^4$ and $R^6$ each denote H; and $R^5$ is $OCH_3$, is excluded.

6. A method of alleviating pain in a mammal comprising administering to said mammal an effective pain-relieving amount of a dimethyl-(3-aryl-but-3-enyl)-amine compound corresponding to formula I

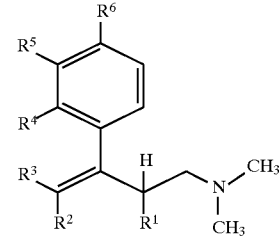

wherein $R^1$ is $C_{1-5}$ alkyl, and $R^2$ denotes H or $C_{1-5}$ alkyl, or $R^1$ and $R^2$ together represent —$(CH_2)_{2-4}$—, —$(CH_2)_2$—$CHR^7$— or —$CH_2$—$CHR^7$—$CH_2$—;

$R^3$ denotes H or $C_{1-5}$ alkyl;

$R^4$ denotes H, OH, $C_{1-4}$ alkyl, O—$C_{1-4}$ alkyl, O-benzyl, $CF_3$, O—$CF_3$, Cl, F or $OR^8$, $R^5$ represents H, OH, $C_{1-4}$ alkyl, O—$C_{1-4}$ alkyl, O-benzyl, $CHF_2$, $CF_3$, O—$CF_3$, Cl, F or $OR^8$, and $R^6$ denotes H, OH, $C_{1-4}$ alkyl, O—$C_{1-4}$ alkyl, O-benzyl, $CF_3$, O—$CF_3$, Cl, F or $OR^8$, with the proviso that two of the radicals $R^4$, $R^5$ or $R^6$ are H, or $R^4$ and $R^5$ together denote —CH=C($R^9$)—O— or —CH=C($R^9$)—S—, with the proviso that $R^6$ is H, or $R^5$ and $R^6$ together denote —CH=CH—C($OR^{10}$)=CH—, with the proviso that $R^4$ is H, $R^7$ denotes $C_{1-8}$ alkyl, $C_{3-8}$ cycloalkyl, O—$C_{1-4}$ alkyl, O-benzyl, $CF_3$, Cl or F, $R^8$ denotes CO—$C_{1-5}$ alkyl, PO(O—$C_{1-4}$ alkyl)$_2$, CO—$C_6H_4$—$R^{11}$, CO(O—$C_{1-5}$ alkyl), CO—$CHR^{12}$—$NHR^{13}$, CO—NH—$C_6H_3$—($R^{14}$)$_2$ or an unsubstituted or substituted pyridyl, thienyl, thiazoyl or phenyl group, $R^9$ denotes H or $C_{1-4}$ alkyl, $R^{10}$ denotes H or $C_{1-3}$ alkyl, $R^{11}$ denotes OC(O)—$C_{1-3}$ alkyl in the ortho position or $CH_2$—N—($R^{15}$)$_2$ in the meta or para position, wherein $R^{15}$ denotes $C_{1-4}$ alkyl or both radicals $R^{15}$ form the 4-morpholino radical together with N, $R^{12}$ and $R^{13}$ each independently represent H, $C_{1-6}$ alkyl or $C_{3-8}$ cycloalkyl, or $R^{12}$ and $R^{13}$ together denote —(CH$_2$)$_{3-8}$—, $R^{14}$ denotes H, OH, $C_{1-7}$ alkyl, O—$C_{1-7}$ alkyl, phenyl, O-aryl, $CF_3$, Cl or F, with the proviso that the two radicals $R^{14}$ are the same or different, or a salt thereof with a physiologically acceptable acid, as an isolated enantiomer or as a racemic mixture, with the proviso that the racemic mixture of the compound of formula I, in which $R^1$ and $R^2$ together represent —(CH$_2$)$_3$—; $R^3$, $R^4$ and $R^6$ each denote H; and $R^5$ is OCH$_3$, is excluded.

* * * * *